US00PP31183P2

(12) United States Plant Patent
Heuger

(10) Patent No.: US PP31,183 P2
(45) Date of Patent: Dec. 3, 2019

(54) ***HELLEBORUS* PLANT NAMED 'COSEH 4900'**

(50) Latin Name: ***Helleborus* x *ericsmithii* X *Helleborus* x *hybridus***
Varietal Denomination: COSEH 4900

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/350,423

(22) Filed: Nov. 15, 2018

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 6/72
See application file for complete search history.

(56) References Cited

PUBLICATIONS

Pluto Plant Variety Database Jun. 4, 2019. p. 1.*

* cited by examiner

*Primary Examiner* — Annette H Para
(74) *Attorney, Agent, or Firm* — C. A. Whealy

(57) ABSTRACT

A new and distinct cultivar of *Helleborus* plant named 'COSEH 4900', characterized by its upright and mounded plant habit; moderately vigorous growth habit; dark green-colored leaves; moderately freely flowering habit; single dark greyed purple-colored flowers; and good garden performance.

2 Drawing Sheets

Botanical designation: *Helleborus* x *ericsmithii* X *Helleborus* x *hybridus*.
Cultivar denomination: 'COSEH 4900'.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 4900'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2014.

Asexual reproduction of the new *Helleborus* plant by divisions in a controlled environment in Glandorf, Germany since May, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4900'. These characteristics in combination distinguish 'COSEH 4900' as a new and distinct *Helleborus* plant:

1. Upright and mounded plant habit.
2. Moderately vigorous growth habit.
3. Dark green-colored leaves.
4. Moderately freely flowering habit.
5. Single dark greyed purple-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have dark greyed purple-colored flowers whereas plants of the female parent selection have cream-colored flowers.

Plants of the new *Helleborus* differ from plants of the male parent selection in the following characteristics:

1. Plants of the new *Helleborus* are taller than plants of the male parent selection.
2. Plants of the new *Helleborus* have darker greyed purple-colored flowers than plants of the male parent selection.

Plants of the new *Helleborus* can be compared to plants of *Helleborus* x *hybridus* 'Annas Red', not patented. In side-by-side comparisons, plants of the new *Helleborus* differ primarily from plants of 'Annas Red' in the following characteristics:

1. Plants of the new *Helleborus* have less distinct leaf venation than plants of 'Annas Red'.

2. Plants of the new *Helleborus* are more freely flowering than plants of 'Annas Red'.
3. Plants of the new *Helleborus* flower earlier than plants of 'Annas Red'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4900' grown in a container.

The photograph on the second sheet is a close-up view of a typical flower of 'COSEH 4900'.

DETAILED BOTANICAL DESCRIPTION

The aforementioned photographs and following observations, measurements and values describe plants grown during November in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 16 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 4900'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro meristem culture.

*Time to initiate roots, winter*.—About 50 days at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous growth habit; moderate growth rate.

*Plant height, soil level to top of foliar plane*.—About 30.5 cm.

*Plant height, soil level to top of flowers*.—About 27.1 cm.

*Plant diameter* (*area of spread*).—About 42.9 cm.

Leaf description:

*Arrangement*.—Leaves arranged in a basal rosette; leaves palmately compound with typically five leaflets per leaf.

*Leaf length*.—About 20.4 cm.

*Leaf width*.—About 22.4 cm.

*Leaflet length*.—About 14.7 cm.

*Leaflet width*.—About 6.4 cm.

*Leaf shape*.—Palmate; reniform in outline.

*Leaflet shape*.—Obovate to elliptic.

*Leaflet apex*.—Acute to apiculate.

*Leaflet base*.—Attenuate.

*Leaflet margin*.—Coarsely serrate; moderately undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 147A; venation, close to 187A. Developing leaflets, lower surface: Close to 148A tinged with close to 197A; midvein, close to 187A. Fully developed leaflets, upper surface: Close to darker than between 139A and N189A; venation, close to 143A. Fully developed leaflets, lower surface: Close to 147B; venation, close to N199A.

*Petioles*.—Length: About 16.8 cm. Diameter: About 6 mm to 8 mm. Strength: Strong. Texture and luster, upper and lower surfaces: Smooth, glabrous; moderately glossy. Color, upper surface: Close to 144A; densely covered with small dots, close to N186C; towards the base, close to N186C. Color, lower surface: Close to between 143A and 144A; densely covered with small dots, close to N186C; towards the base, close to N186C.

Flower description:

*Flower shape and habit*.—Single rotate flowers; arranged solitary or in clusters with about three flowers each; moderately freely flowering habit with about 29 flowers developing per plant; flowers facing outwardly to nodding.

*Fragrance*.—None detected.

*Natural flowering season*.—Plants begin flowering about ten months after planting; plants flower during the late autumn into the winter in Germany.

*Flower longevity on the plant*.—About ten days; sepals persistent, other flower parts are not persistent.

*Flower buds*.—Length: About 2.5 cm. Diameter: About 1.5 cm. Shape: Broadly ovoid. Texture and luster: Smooth, glabrous; matte. Color: Close to 59B, N7713 and 187C.

*Inflorescence height*.—About 27.1 cm.

*Inflorescence diameter*.—About 20.8 cm.

*Flower diameter*.—About 10.3 cm.

*Flower depth* (*height*).—About 3.1 cm.

*Petals*.—Transformed into nectaries.

*Sepals*.—Quantity and arrangement: About five, arranged in a single whorl. Length: About 5.7. cm. Width: About 4.7 cm. Shape: Broadly ovate, slightly concave. Apex: Obtuse. Base: Cuneate. Margin: Entire; moderately undulate. Texture and luster, upper surface: Smooth, glabrous; matte. Texture and luster, lower surface: Smooth, glabrous; slightly glossy. Color: When opening, upper surface: Close to 59B tinged towards the margins with close to 187B. When opening, lower surface: Close to between 59B and N79C tinged towards the margins with close to 187B. Fully opened, upper surface: Close to N186D tinged towards the margins with close to N79A. Fully opened, lower surface: Close to N79A and N79B.

*Flower bracts*.—Quantity per flower: Typically two. Length: About 11 cm. Width: About 5.2 cm. Shape: Elliptic. Apex: Acute. Base: Cuneate. Margin: Distally, shallowly serrate; proximally, entire; strongly undulate. Color, upper surface: Darker than between NN137A and 147A. Color, lower surface: Close to 147B; venation, close to N186C.

*Peduncles*.—Length: About 22.4 cm. Diameter: About 0.8 cm to 1.2 cm. Aspect: About 10° from vertical. Strength: Strong. Texture and luster: Smooth, glabrous; moderately glossy. Color: Close to 144A to 144B; flushed with close to 187B to 187C; fine dots, close to 187B to 187C.

*Pedicels*.—Length: About 7.9 cm. Diameter: About 3.5 mm to 4 mm. Aspect: About 25° from peduncle axis. Strength: Moderately strong. Texture and luster: Smooth, glabrous; moderately glossy. Color: Close to 187B; fine dots, close to 144A.

*Reproductive organs*.—Stamens: Quantity per flower: About 120. Filament length: About 2 cm. Filament color: Close to 186B fading distally to close to NN155D. Anther shape: Reniform; basifixed. Anther size: About 2 mm by 3 mm. Anther color: Close to 4B. Pollen amount: Scarce. Pollen color: Close to 4D. Pistils: Quantity per flower: About four. Pistil length: About 1.3 cm. Stigma diameter: About 0.3 mm. Stigma shape: Club-shaped. Stigma color: Close to 145D. Style length: About 1.25 cm. Style color: Close to 187C. Ovary color: Close to 187A to 187B. Nectaries (transformed petals): Quantity per flower: About 13. Length: About 1.2 cm. Diameter: About 4 mm. Shape: Tubular, flattened. Texture and luster, inner and outer surfaces: Smooth, glabrous; matte. Color, immature, inner and outer surfaces: Close to 144C. Color, mature, inner and outer surfaces: Close to 144B; distally, close to N144A; main color becoming closer to 144A with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 4900' as illustrated and described.

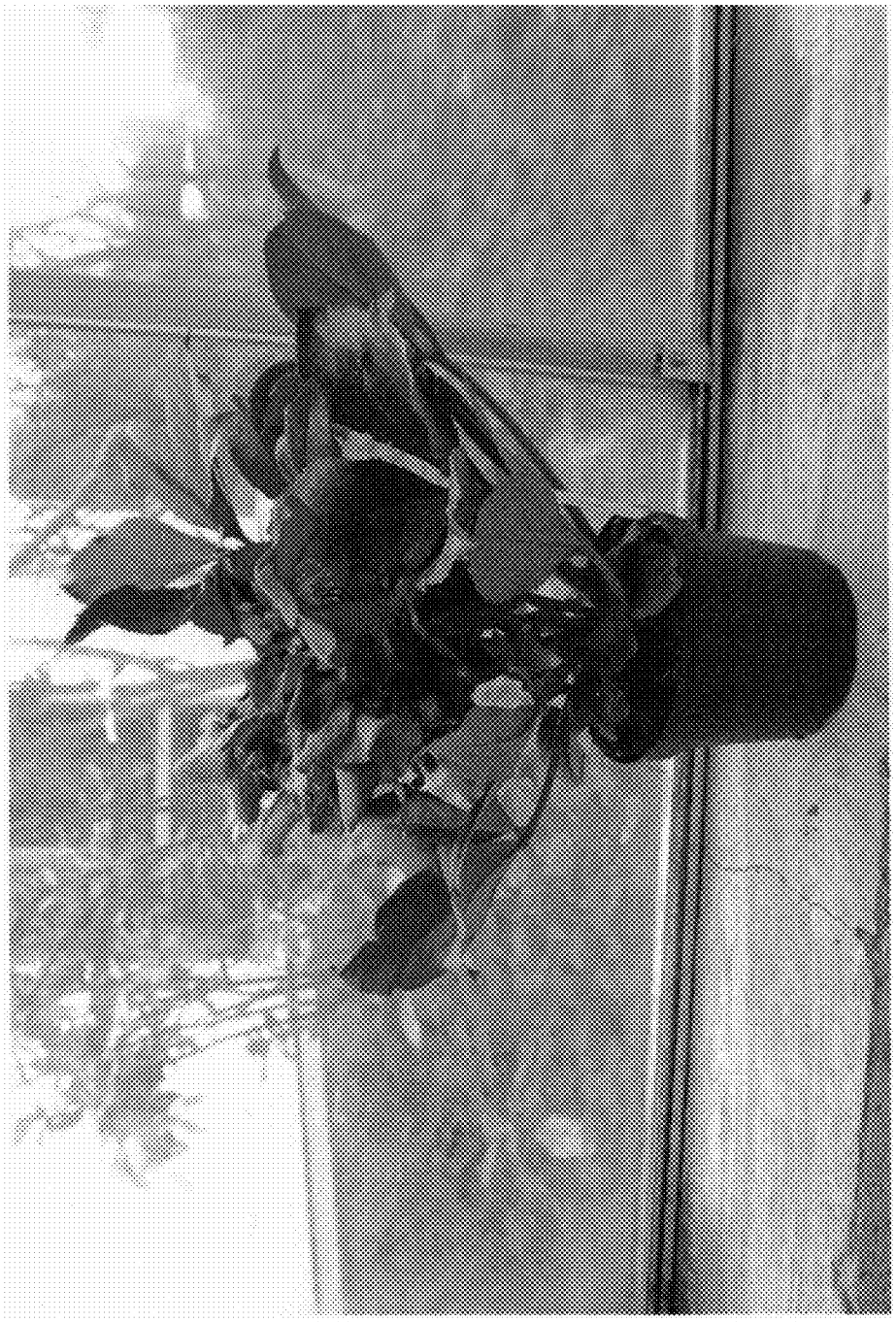

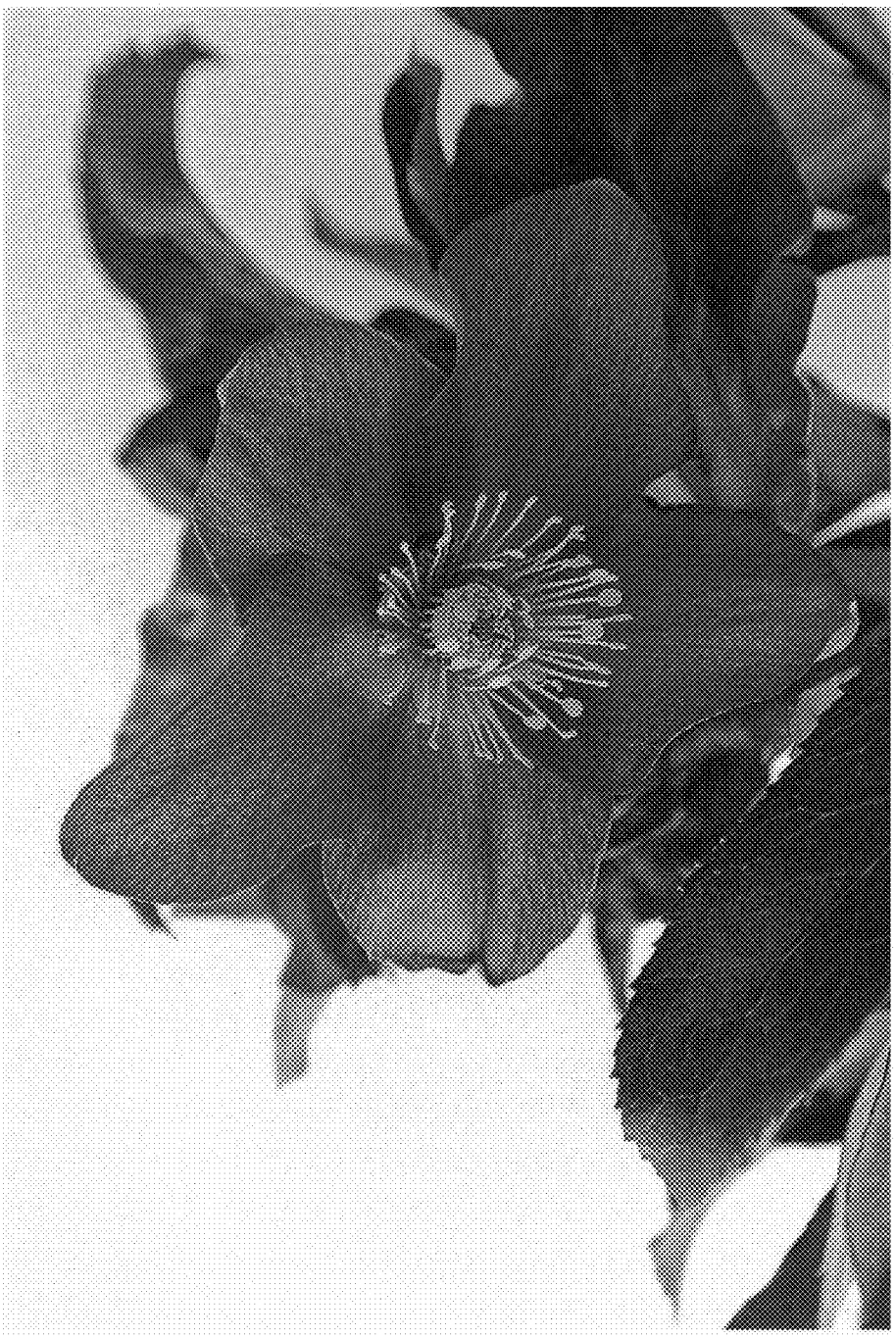

* * * * *